(12) United States Patent
Bieberich et al.

(10) Patent No.: US 9,310,257 B2
(45) Date of Patent: Apr. 12, 2016

(54) DEEP TISSUE TEMPERATURE PROBE CONSTRUCTIONS

(75) Inventors: Mark T. Bieberich, Edina, MN (US); Albert P. Van Duren, Chaska, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 1000 days.

(21) Appl. No.: 12/798,945

(22) Filed: Apr. 14, 2010

(65) Prior Publication Data

US 2010/0268113 A1 Oct. 21, 2010

Related U.S. Application Data

(60) Provisional application No. 61/212,749, filed on Apr. 15, 2009.

(51) Int. Cl.
| | |
|---|---|
| *A61B 19/00* | (2006.01) |
| *G01K 1/16* | (2006.01) |
| *A61B 5/01* | (2006.01) |
| *A61B 5/00* | (2006.01) |
| *G01K 13/00* | (2006.01) |

(52) U.S. Cl.
CPC . *G01K 1/165* (2013.01); *A61B 5/01* (2013.01); *A61B 5/6833* (2013.01); *A61B 5/6843* (2013.01); *G01K 1/16* (2013.01); *G01K 13/002* (2013.01); *A61B 2562/0271* (2013.01); *A61B 2562/0276* (2013.01); *A61B 2562/164* (2013.01)

(58) Field of Classification Search
USPC .......... 136/211, 212, 225; 206/306; 374/134, 374/163, 169, 209, 29, 30, 44; 600/549; 607/108; 702/131
See application file for complete search history.

(56) References Cited

U.S. PATENT DOCUMENTS

| | | | |
|---|---|---|---|
| 1,363,259 A | 12/1920 | Mills | |
| 1,526,641 A | 2/1925 | Mulvany et al. | |
| 1,528,383 A | 3/1925 | Schmidt | |
| 1,638,943 A | 8/1927 | Little | |
| 2,378,804 A | 6/1945 | Sparrow et al. | |
| 2,381,819 A | 8/1945 | Graves et al. | |
| 2,519,785 A | 8/1950 | Okolicsanyi | |
| 2,629,757 A | 2/1953 | McKay | |
| 2,807,657 A | 9/1957 | Jenkins et al. | ................... 136/4 |

(Continued)

FOREIGN PATENT DOCUMENTS

| | | | | |
|---|---|---|---|---|
| CA | 2 538 940 A1 | 6/2006 | ............... | A61B 5/00 |
| CA | 2 583 034 A1 | 9/2007 | ............... | A61B 5/01 |

(Continued)

OTHER PUBLICATIONS

International Search Report and Written Opinion, PCT/US2011/000549, mailed Jun. 26, 2011.

(Continued)

*Primary Examiner* — Sean Dougherty
(74) *Attorney, Agent, or Firm* — X. Christina Huang (57) ABSTRACT

Disposable, zero-heat-flux, deep tissue temperature probes are constructed using a support assembly constituted of a flexible substrate that supports elements of the probe. One support assembly embodiment includes a folded substrate with a heater and thermal sensors disposed on it. Another support assembly includes multiple sections separable into strata supporting a covering guard heater, a central thermal sensor, and a thermal sensor displaced at least radially from the central thermal sensor.

9 Claims, 5 Drawing Sheets

(56) References Cited

U.S. PATENT DOCUMENTS

| | | | | |
|---|---|---|---|---|
| 2,969,141 | A | 1/1961 | Katzin | 206/16.5 |
| 3,099,575 | A | 7/1963 | Hill | 117/212 |
| 3,099,923 | A | 8/1963 | Benzinger | 73/341 |
| 3,215,265 | A | 11/1965 | Welin-Berger | 206/63.2 |
| 3,235,063 | A | 2/1966 | Jarund | 206/16.5 |
| 3,238,775 | A | 3/1966 | Watts | 73/190 |
| 3,301,394 | A | 1/1967 | Baermann et al. | 206/63.2 |
| 3,367,182 | A | 2/1968 | Baxter | 73/190 |
| 3,427,209 | A | 2/1969 | Hager, Jr. | 136/225 |
| 3,469,685 | A | 9/1969 | Baermann | 206/63.2 |
| 3,552,558 | A | 1/1971 | Poncy | 206/63.2 |
| 3,581,570 | A | 6/1971 | Wortz | 73/355 R |
| 3,607,445 | A | 9/1971 | Hines | 136/225 |
| 3,720,103 | A | 3/1973 | Adams et al. | 73/190 H |
| 3,767,470 | A | 10/1973 | Hines | 136/225 |
| 3,781,749 | A | 12/1973 | Iles et al. | 338/25 |
| 3,809,230 | A | 5/1974 | Poncy | 206/306 |
| 3,833,115 | A | 9/1974 | Schapker | 206/63.2 |
| 3,877,463 | A | 4/1975 | Cary et al. | 128/2 H |
| 3,933,045 | A | 1/1976 | Fox et al. | 73/359 |
| 3,942,123 | A | 3/1976 | Georgi | 328/1 |
| 4,022,063 | A | 5/1977 | West et al. | 73/362 |
| 4,024,312 | A | 5/1977 | Korpman | 428/343 |
| 4,142,631 | A | 3/1979 | Brandriff | 206/306 |
| 4,190,058 | A | 2/1980 | Sagi | |
| 4,253,469 | A | 3/1981 | Aslan | 128/736 |
| 4,275,741 | A | 6/1981 | Edrich | 128/653 |
| 4,347,854 | A | 9/1982 | Gosline et al. | 128/736 |
| 4,407,292 | A | 10/1983 | Edrich | 128/653 |
| 4,494,550 | A | 1/1985 | Blazek et al. | 128/664 |
| 4,539,994 | A | 9/1985 | Baumbach et al. | 128/635 |
| 4,541,734 | A | 9/1985 | Ishizaka | 374/169 |
| 4,572,213 | A | 2/1986 | Kawahara | 128/736 |
| 4,574,359 | A | 3/1986 | Ishizaka et al. | 364/557 |
| 4,577,976 | A | 3/1986 | Hayashi et al. | 374/29 |
| 4,592,000 | A | 5/1986 | Ishizaka et al. | 364/557 |
| 4,629,336 | A | 12/1986 | Ishizaka | 364/557 |
| 4,648,055 | A | 3/1987 | Ishizaka et al. | 364/557 |
| 4,652,145 | A | 3/1987 | Bjornberg | 374/194 |
| 4,669,049 | A | 5/1987 | Kosednar et al. | 364/557 |
| 4,747,413 | A | 5/1988 | Bloch | 128/736 |
| 4,841,543 | A | 6/1989 | Dittmar et al. | 374/44 |
| 4,859,078 | A | 8/1989 | Bowman et al. | 374/44 |
| 4,899,297 | A | 2/1990 | Sano et al. | 364/557 |
| 4,955,380 | A | 9/1990 | Edell | 128/653 |
| 4,987,579 | A | 1/1991 | Yoshinaka et al. | 377/25 |
| 5,002,057 | A | 3/1991 | Brady | 128/652 |
| 5,015,102 | A | 5/1991 | Yamaguchi | 374/107 |
| 5,033,866 | A | 7/1991 | Kehl et al. | 374/179 |
| 5,040,901 | A | 8/1991 | Suzuki | 374/183 |
| 5,050,612 | A | 9/1991 | Matsumura | 128/670 |
| 5,062,432 | A | 11/1991 | James et al. | 128/736 |
| 5,088,837 | A | 2/1992 | Shiokawa et al. | 374/185 |
| 5,149,200 | A | 9/1992 | Shiokawa et al. | 374/185 |
| 5,172,979 | A | 12/1992 | Barkley et al. | 374/147 |
| 5,178,468 | A | 1/1993 | Shiokawa et al. | 374/185 |
| 5,199,436 | A | 4/1993 | Pompei et al. | 128/664 |
| 5,255,979 | A | 10/1993 | Ferrari | 374/158 |
| 5,263,775 | A | 11/1993 | Smith et al. | 374/179 |
| 5,293,877 | A | 3/1994 | O'Hara et al. | 128/736 |
| 5,483,190 | A | 1/1996 | McGivern | 327/34 |
| 5,516,581 | A | 5/1996 | Kreckel et al. | 428/317.3 |
| 5,816,706 | A | 10/1998 | Heikkila et al. | 374/134 |
| 5,884,235 | A | 3/1999 | Ebert | 702/87 |
| 5,990,412 | A | 11/1999 | Terrell | 136/225 |
| 5,993,698 | A | 11/1999 | Frentzel et al. | 252/511 |
| 6,001,471 | A | 12/1999 | Bries et al. | 428/343 |
| 6,014,890 | A | 1/2000 | Breen | 73/29.02 |
| 6,019,507 | A | 2/2000 | Takaki | 374/161 |
| 6,059,452 | A | 5/2000 | Smith et al. | 374/169 |
| 6,203,191 | B1 | 3/2001 | Mongan | 374/43 |
| 6,220,750 | B1 | 4/2001 | Palti | 374/164 |
| 6,224,543 | B1 | 5/2001 | Gammons et al. | 600/124 |
| 6,231,962 | B1 | 5/2001 | Bries et al. | 428/317.3 |
| 6,253,098 | B1 | 6/2001 | Walker et al. | 600/344 |
| 6,255,622 | B1 | 7/2001 | May et al. | 219/209 |
| 6,278,051 | B1 | 8/2001 | Peabody | 136/225 |
| 6,280,397 | B1 | 8/2001 | Yarden et al. | 600/549 |
| 6,283,632 | B1 | 9/2001 | Takaki | 374/161 |
| 6,292,685 | B1 | 9/2001 | Pompei | 600/474 |
| 6,300,554 | B1 * | 10/2001 | Du et al. | 136/201 |
| 6,312,391 | B1 | 11/2001 | Ramadhyani et al. | 600/549 |
| 6,355,916 | B1 | 3/2002 | Siefert | 219/494 |
| 6,377,848 | B1 | 4/2002 | Garde et al. | 604/20 |
| 6,398,727 | B1 | 6/2002 | Bui et al. | 600/300 |
| 6,495,806 | B2 | 12/2002 | Siefert | 219/494 |
| 6,553,243 | B2 | 4/2003 | Gurley | 600/340 |
| 6,595,929 | B2 | 7/2003 | Stivoric et al. | 600/549 |
| 6,626,037 | B1 * | 9/2003 | Wado | G01F 1/6845 73/204.11 |
| 6,676,287 | B1 | 1/2004 | Mathis et al. | 374/1 |
| 6,773,405 | B2 | 8/2004 | Fraden et al. | 600/549 |
| 6,827,487 | B2 | 12/2004 | Baumbach | 374/164 |
| 6,886,978 | B2 | 5/2005 | Tokita et al. | 374/169 |
| 6,929,611 | B2 | 8/2005 | Koch | 600/549 |
| 7,059,767 | B2 | 6/2006 | Tokita et al. | 374/163 |
| 7,270,476 | B2 | 9/2007 | Tokita et al. | 374/107 |
| 7,276,076 | B2 * | 10/2007 | Bieberich | 607/108 |
| 7,299,090 | B2 | 11/2007 | Koch | 600/547 |
| 7,306,283 | B2 | 12/2007 | Howick et al. | 297/180.12 |
| 7,318,004 | B2 | 1/2008 | Butterfield | 702/130 |
| 7,354,195 | B2 | 4/2008 | Sakano | 374/208 |
| 7,364,356 | B2 | 4/2008 | Dicks et al. | 374/121 |
| 7,410,291 | B2 | 8/2008 | Koch | 374/163 |
| 7,426,872 | B2 | 9/2008 | Dittmar et al. | 73/818 |
| 7,470,280 | B2 * | 12/2008 | Bieberich | 607/104 |
| 8,025,690 | B2 * | 9/2011 | Bieberich | 607/108 |
| 8,123,790 | B2 * | 2/2012 | Bieberich | 607/107 |
| 8,123,792 | B2 * | 2/2012 | Bieberich | 607/108 |
| 8,226,294 | B2 * | 7/2012 | Bieberich et al. | 374/163 |
| 8,292,495 | B2 * | 10/2012 | Bieberich et al. | 374/1 |
| 8,292,502 | B2 * | 10/2012 | Bieberich et al. | 374/163 |
| 2002/0097775 | A1 | 7/2002 | Hamouda et al. | 374/29 |
| 2003/0130590 | A1 | 7/2003 | Bui et al. | 600/537 |
| 2004/0210280 | A1 | 10/2004 | Liedtke | 607/96 |
| 2005/0245839 | A1 | 11/2005 | Stivoric et al. | 600/549 |
| 2007/0167859 | A1 | 7/2007 | Finneran et al. | 600/546 |
| 2007/0206655 | A1 | 9/2007 | Haslett et al. | 374/141 |
| 2007/0282218 | A1 | 12/2007 | Yarden | 600/549 |
| 2008/0170600 | A1 | 7/2008 | Sattler et al. | 374/163 |
| 2008/0264166 | A1 * | 10/2008 | Wienand | G01F 1/6845 73/204.26 |
| 2009/0129433 | A1 | 5/2009 | Zhang et al. | 374/102 |
| 2010/0121217 | A1 * | 5/2010 | Padiy et al. | 600/549 |
| 2010/0292605 | A1 | 11/2010 | Grassl et al. | 600/549 |
| 2011/0051776 | A1 * | 3/2011 | Bieberich et al. | 374/163 |
| 2011/0249699 | A1 * | 10/2011 | Bieberich et al. | 374/1 |
| 2011/0249701 | A1 * | 10/2011 | Bieberich et al. | 374/163 |
| 2012/0289855 | A1 * | 11/2012 | Bieberich et al. | 600/549 |
| 2013/0010828 | A1 * | 1/2013 | Bieberich et al. | 374/163 |

FOREIGN PATENT DOCUMENTS

| | | | | |
|---|---|---|---|---|
| DE | 3527942 | A1 | 2/1987 | G01K 7/00 |
| EP | 0239824 | B1 | 5/1992 | G01K 13/00 |
| GB | 2266771 | A | 11/1993 | G01K 1/18 |
| JP | 55-29794 | | 3/1980 | G01K 1/16 |
| JP | 57-183832 | | 12/1982 | A61B 5/00 |
| JP | 08-211000 | | 8/1996 | G01N 25/00 |
| JP | 2002202205 | A | 7/2002 | G01K 7/00 |
| JP | 2007-212407 | A | 8/2007 | A61B 5/01 |
| JP | 2009-080000 | A | 4/2009 | A61B 5/04 |
| WO | WO 99/60356 | A1 | 11/1999 | G01K 17/00 |
| WO | WO 00/58702 | A1 | 10/2000 | G01K 7/02 |
| WO | WO 01/31305 | A1 | 5/2001 | G01K 7/42 |
| WO | WO 02/066946 | A2 | 8/2002 | G01K 13/00 |
| WO | WO 2007/060609 | A2 | 5/2007 | A61B 5/0408 |
| WO | WO 2008/068665 | A1 | 6/2008 | G01K 1/16 |
| WO | WO 2008068665 | A1 * | 6/2008 | G01K 1/16 |
| WO | WO 2008/078271 | A1 | 7/2008 | G01K 1/16 |
| WO | WO 2009/141780 | A1 | 11/2009 | G01K 1/16 |
| WO | WO 2010/082102 | A2 | 7/2010 | G01K 1/14 |
| WO | WO 2010/103436 | A1 | 9/2010 | G01K 1/16 |
| WO | WO 2010/116297 | A1 | 10/2010 | G01K 1/14 |

(56) References Cited

FOREIGN PATENT DOCUMENTS

| WO | WO 2010/120360 A1 | 10/2010 | ............ G01K 13/00 |
| WO | WO 2010/120362 A1 | 10/2010 | ............ G01K 13/00 |
| WO | WO 2011/025521 A1 | 10/2010 | |
| WO | WO 2011/126543 A1 | 10/2011 | |
| WO | WO 2011/146098 A1 | 11/2011 | |

OTHER PUBLICATIONS

International Search Report and Written Opinion, PCT/US2011/000552, mailed Jun. 29, 2011.
Fox RH, et al, A new technique for monitoring the deep body temperature in man from the intact skin surface. *J. Physiol.* 1971; 212(2): 8P-10P.
Solman AJ, et al, New thermometers for deep tissue temperature. *Biomedical Engineering* 1973; 8(10): 432-435.
Fox RH, et al, A new method for monitoring deep body temperature from the skin surface. *Clin. Sci.* 1973; 44: 81-86.
Togawa, T, et al, A modified internal temperature measurement device, *Medical and Biological Engineering*, May 1976, pp. 361-364.
Togawa T, Non-invasive deep body temperature measurement. In: Rolfe P (ed) *Non-invasive Physiological Measurements*. 1979; vol. 1: 261-277.
Zhang X, et al, Application of the Heat Flux Meter in Physiological Studies, *J. therm. Biol.*, 1993, vol. 18: 473-476. Yamakage M, et al, Deep temperature monitoring-comparative study between conventional and new developed monitors, *Anesthesiology*, 2002; 96: A501.
Suleman M-I, et al, Insufficiency in a new temporal-artery thermometer for adult and pediatric patients, *Anesth Analg*, 2002; 95: 67-71.
Yamakage M, Evaluation of a newly developed monitor of deep body temperature, *J. Anesth.*, 2002; 16:354-357.
Thurbide, K., Excuse me, but my Band-Aid is beeping, Haslett's smart Band-Aid/University of Calgary, Jul. 18, 2007, pp. 1-2.
Gunga H-C, et al, A non-invasive device to continuously determine heat strain in humans. *J. Ther. Bio.* 2008; 33: 297-307.
Kimberger O, Accuracy and precision of a novel non-invasive core thermometer. *B.JA.* 2009; 103(2): 226-231.
Langham GE, et al, Noninvasive temperature monitoring in postanesthesia care units, *Anesthesiology*, 2009, 111; 1:1-7.
Kitamura, K, et al, Development of a new method for the noninvasive measurement of deep body temperature without a heater, *Med. Eng. Phys.*, 2010; 32(1): 1-6. Epub Nov. 10, 2009.
Zeiner A, et al, Non-invasive continuous cerebral temperature monitoring in patients treated with mild therapeutic hypothermia: an observational pilot study, *Resuscitation*, Jul. 2010; 81(7) 861-866. Epub Apr. 15, 2010.
International Search Report and Written Opinion, PCT/US2010/001108, mailed Jul. 23, 2010.
International Search Report and Written Opinion, PCT/US2010/001104, mailed Jul. 26, 2010.
International Search Report and Written Opinion, PCT/US2010/002185, mailed Dec. 13, 2010.

\* cited by examiner

DEEP TISSUE TEMPERATURE PROBE CONSTRUCTIONS

PRIORITY

This application claims priority to U.S. Provisional Application for patent 61/212,749 filed Apr. 15, 2009.

RELATED APPLICATIONS

This application contains material related to the following US patent applications:
U.S. patent application Ser. No. 12/584,108, filed Aug. 31, 2009.

BACKGROUND

The subject matter relates to a temperature probe-a device placed on the skin of a subject to measure temperature. More particularly, the subject matter pertains to a deep tissue temperature (DTT) probe. Deep tissue temperature measurement is a non-invasive determination of the core temperature of a human body in which a probe is located over a region of deep tissue that is representative of the body core. The probe reads the temperature of that region as the core temperature.

Figure 1:
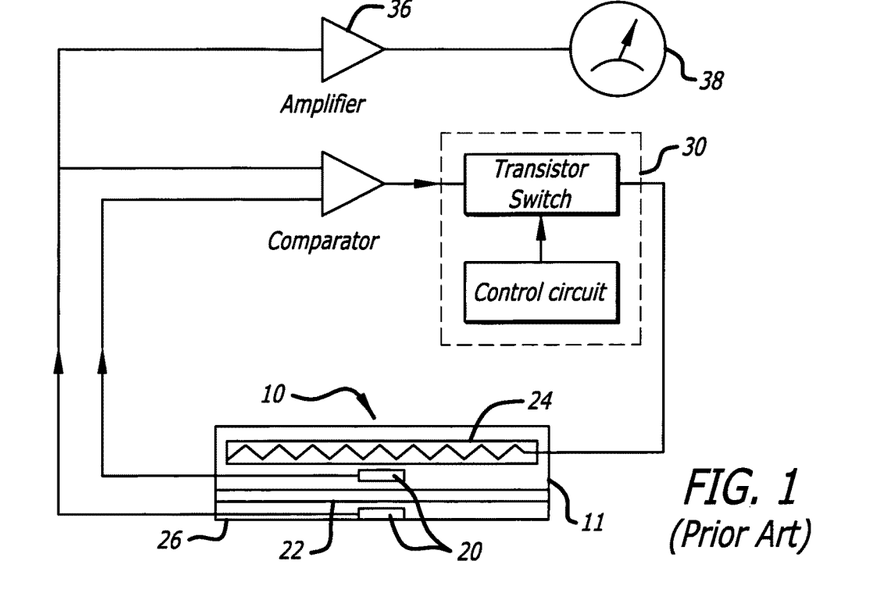
FIG. 1 is a schematic block diagram of a first prior art deep tissue temperature measurement system including a ZHF deep tissue temperature probe.

A system for non-invasively measuring deep tissue temperature was described by Fox and Solman in 1971 (Fox R H, Solman A J. A new technique for monitoring the deep body temperature in man from the intact skin surface. J. Physiol. January 1971:212(2): pp 8-10). The system, illustrated in FIG. 1, estimates body core temperature by indirect means using a specially designed probe 10 that stops or blocks heat flow through a portion of the skin. The components of the probe 10 are contained in a housing 11. The probe 10 includes two thermistors 20 mounted on either side of a thermal resistance 22, which may be constituted of a layer of insulating material capable of supporting the thermistors 20. The probe 10 also includes a heater 24 disposed at the top of the probe 10, over the elements 20, 22, and 24. In use, the probe 10 is placed on a region of skin where deep tissue temperature is to be measured. With the bottom surface 26 of the probe resting on a person's body, in contact with the skin, the thermistors 20 measure a temperature difference, or error signal, across the thermal resistance 22. The error signal is used to drive a heater controller 30, which, in turn, operates to minimize the error signal by causing the heater 24 to provide just enough heat to equalize the temperature on both sides of the thermal resistance 22. When the temperatures sensed by the thermistors 20 are equal, there is no heat flow through the probe, and the temperature measured by the lower thermistor 20 by way of a temperature meter circuit constituted of an amplifier 36 and a temperature meter 38 is equivalent to DTT. The probe 10 essentially acts as a thermal insulator that blocks heat flow through the thermal resistor 22; DTT probes that operate in the same manner are termed "zero-heat-flux" ("ZHF") probes. Since the heater 24 operates to guard against loss of heat along the path of measurement through the probe, it is often referred to as a "guard heater".

Figure 2:
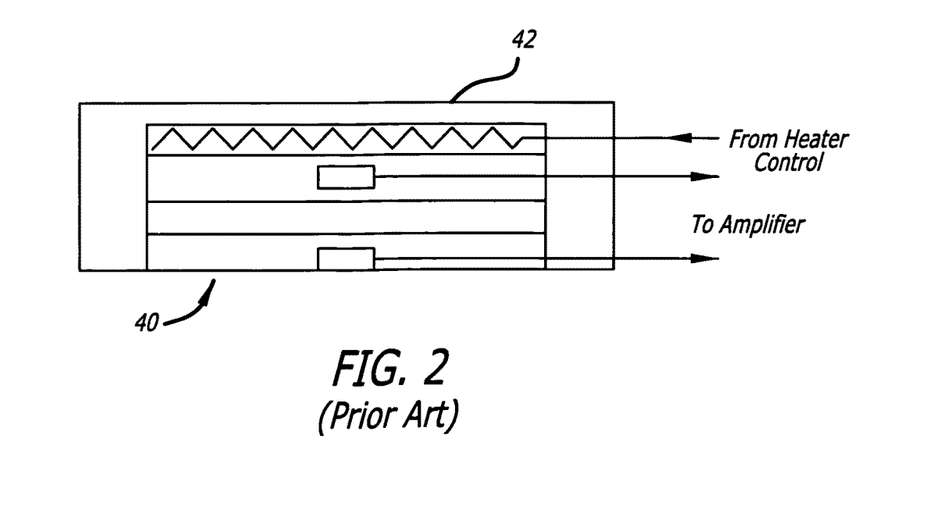
FIG. 2 is a schematic side sectional diagram of a second prior art deep tissue temperature measurement system including a ZHF deep tissue temperature probe with an aluminum cap.

Togawa improved the Fox/Solman design with a DTT probe structure that accounted for the strong multi-dimensional heat transfer of dermal blood flow through the skin. (Togawa T. Non-Invasive Deep Body Temperature Measurement. In: Rolfe P (ed) Non-Invasive Physiological Measurements. Vol. 1. 1979. Academic Press, London, pp. 261-277). The probe, illustrated in FIG. 2, encloses a ZHF sensor design 40, which blocks heat flow normal to the body, in a thick aluminum housing 42 with a disk-like construction that also reduces or eliminates radial heat flow from the center to the periphery of the probe.

Both Fox/Solman and Togawa use heat flux normal to the body (and the skin where the probe is placed) to control the operation of a heater that blocks heat flow through a thermal resistance. This results in a construction that stacks probe components, which gives the probe a substantial vertical profile. The thermal mass added by Togawa's probe design also improves the stability of the Fox/Solman design. Basic engineering for heat flux measurement would suggest that a large thermal resistance in the probe makes the measurement more accurate, but also slows the transient response rate. Since the goal is zero heat flux across the gage the more thermal resistance the better. However, additional thermal resistance adds mass and size.

Maintenance of body core temperature in a normothermic range during a perioperative cycle has been shown to reduce the incidence of surgical site infection, and so it is beneficial to monitor a patient's body core temperature before, during, and after surgery. Of course non-invasive measurement is very desirable, for both the comfort and the safety of a patient. Deep tissue temperature measurement using a probe supported on the skin provides an accurate and non-invasive means for monitoring body core temperature. However, the size and mass of the Fox/Solman and Togawa probes do not promote disposability. Consequently, they must be sterilized after each use, and stored for reuse. As a result, use of these probes to measure deep tissue temperature may raise the costs associated with DTT measurement and may increase the risk of cross contamination between patients. It is therefore useful to reduce the size and mass of a DTT probe, without sacrificing its performance, in order to promote disposability.

SUMMARY

Disposable, zero-heat-flux, deep tissue temperature probes are constructed using an assembly constituted of a flexible substrate that supports elements of the probe. One support assembly embodiment includes a layer with a multi-zone heater, thermal sensors, and a thermal resistor disposed on it. The heater has multiple zones defined by openings formed through the layer, between the zones, to enhance the flexibility of the probe. Another support assembly includes multiple layers supporting a covering guard heater, a central thermal sensor, and a thermal sensor displaced at least radially from the central thermal sensor.

DETAILED DESCRIPTION OF THE PREFERRED EMBODIMENTS

It is desirable that zero-heat-flux, deep tissue temperature probe (DTT probe) constructions be disposable. Thus the constructions should be easy and inexpensive to fabricate and assemble, have a low mass and a low profile, and comprise inexpensive materials and parts.

It is particularly desirable that disposable DTT constructions be assembled from low-profile, light weight, flexible assemblies that enable zero-heat-flux measurement at various locations on a human or animal body.

A thermal measurement support assembly for zero-heat-flux deep tissue temperature probe (DTT probe) constructions includes a flexible substrate with at least two thermal sensors disposed in a spaced-apart relationship and separated by one or more layers of thermally insulating material. Preferably the sensors are spaced apart vertically as in FIGS. 1 and 2, and they may further be spaced apart horizontally or radially with respect to a center of measurement of vertical heat flux. The substrate supports at least the thermal sensors and the separating thermal insulating material, and it may also support one or more heaters. Once constructed, the support assembly is ready to be incorporated into the structure of a DTT probe.

Figure 3A:
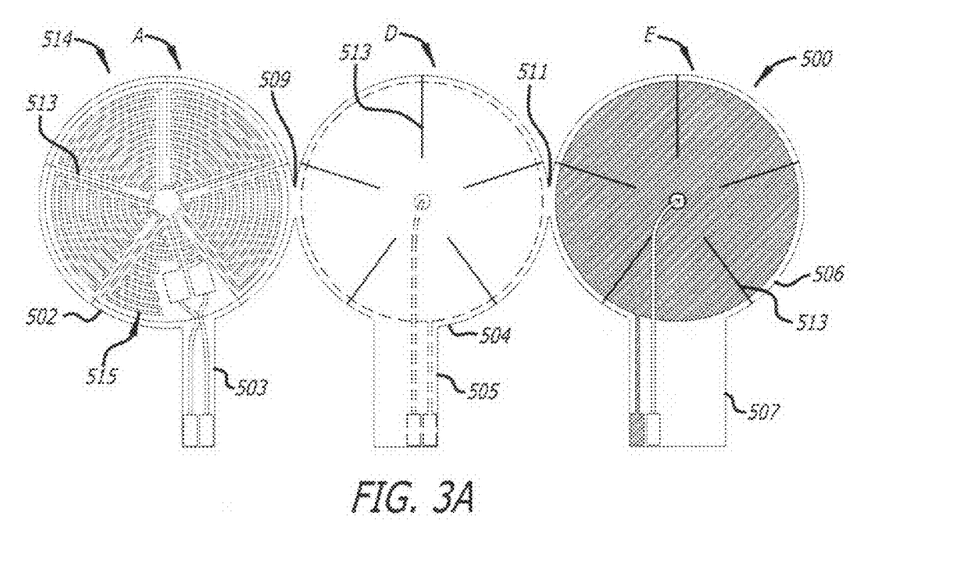
FIGS. 3A-3D illustrate layout and assembly of a first embodiment of a thermal measurement support assembly with a multi-zone heater for a ZHF probe.
Figure 3B:
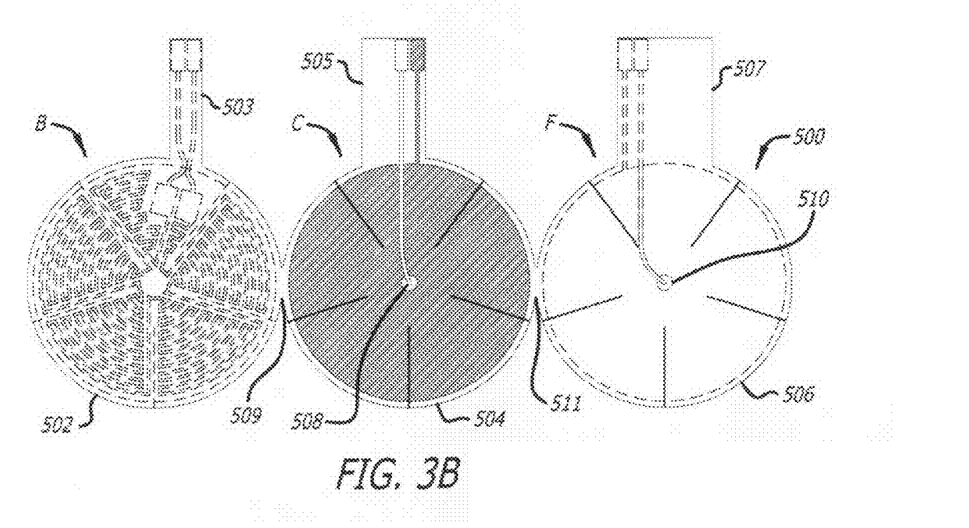

Support assembly constructions illustrated in FIGS. 3A and 3B include a plurality of layers to support a heater and thermal sensors. The layers have multiple zones with slits formed through the layers, between the zones, to enhance the flexibility of the probe. The slits enable the zones to flex independently of one another.

As seen in FIGS. 3A and 3B, a support assembly 500 includes a flexible substrate, preferably a sheet of flexible, thermally insulative material that is formed to include a plurality of contiguous sections. For example three contiguous paddle-shaped sections with disks 502, 504, and 506 of equal diameter are formed and aligned so that their centers lie on a straight line. Each disk transitions to a tab for supporting one or more electrical leads. The tabs are indicated by reference numerals 503, 505, and 507, respectively. The inner periphery of each disk is continuous with each adjacent inner periphery at a point that is tangent to the perimeter of the inner circle and which intersects the line upon which the centers are aligned. Thus, the inner periphery of the outer disk 502 is continuous with the periphery of the inner disk 504 at 509, and the inner periphery of the outer disk 506 is continuous with the periphery of the inner disk 504 at 511, which is diametrically opposite 509 on the periphery of the inner disk 504. Each disk has two opposite-facing, disk-shaped major surfaces. Thus, the outer disk 502 has major surfaces A and B, the inner disk 504 has major surfaces C and D, and the outer 506 has surfaces E and F. The major surfaces A, D, and E are on one side of the support assembly 500; the major surfaces B, C, and F are on the opposite side. Each of the sections is divided into a circular array of wedge-shaped zones by a pattern of radial slits 513 that extend from the circumferential periphery toward the center of each disk. The slits 513 extend up to an undivided central portion of each disk. The slit patterns are identical so that the slits of each section align with the slits of the other sections when the sections are folded together.

As seen in FIGS. 3A and 3B, a heater 514 is supported on the major surface A. Preferably, the heater 514 is constituted of a trace pattern of etched copper which in each wedge-shaped zone contains a corresponding wedge-shaped zone 515 of the heater 514. In order to maximize the thermal capacity of the heater, the heater trace pattern describes a series of switchbacks in each zone, with the connections between zones traversing the un-slitted central portion of the section. The etching includes formation of leads and pins for the heater on the tab 503. The etching also includes formation of rings of exposed insulative material at the peripheries of the major surfaces A, C and E. The disk of copper film inside the ring on the surface C may be used as one element of a thermocouple. For example, a thermocouple junction 508 may be assembled by soldering, brazing, or welding one end of an insulated chromel wire to the copper film, preferably, but not necessarily, at or near the center of the surface C. The other end of the chromel wire is soldered, brazed, or welded to a chromel electrode mounted to the tab 505. Another thermocouple junction 510 may be similarly assembled on the major surface E. Copper is etched from the major surfaces B, D, and F so that those surfaces have no copper thereon.

Figure 3C:
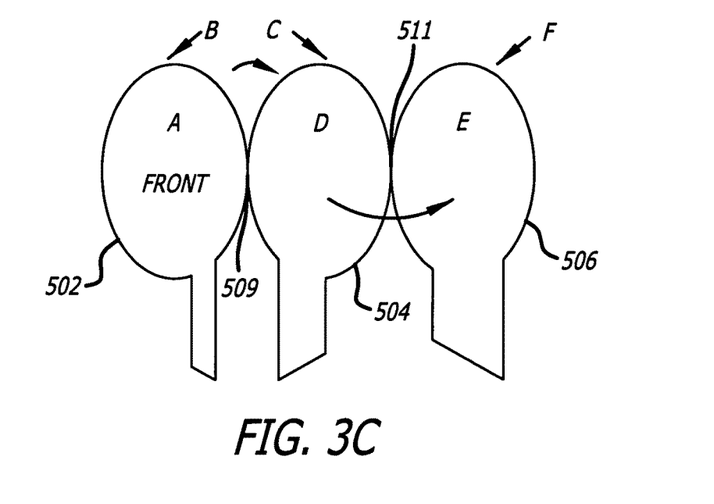

With the heater and thermocouple junctions thus formed, the support assembly 500 may be Z-folded as shown in FIG. 3C. Preferably, the sections 502 and 504 are folded at 509 by swinging the major surfaces B and C together and the sections 504 and 506 are folded at 511 by swinging the major surfaces D and E together. The folded support assembly is seen in the top plan view of FIG. 3D. In this aspect, the support assembly 500 is preferably oriented with respect to a location on a body where a deep tissue temperature reading is to be taken by denominating the heater as the top of the assembly, and major surface F as the bottom. In this aspect, the tabs 503, 505, and 507 are aligned by the folding so as to position all of the leads and pins on a single side of a composite tab 520. Preferably, but not necessarily, the composite tab 520 is oriented with the aligned pins facing in the same direction as the heater on major surface A. Table I below sets forth the pin assignments. In the table, the lower thermocouple is on major surface E and the upper thermocouple is on major surface C. The connectors on the composite tab 520 provide electrical access to each of the thermal sensors and to the heater. A compression connector may be attached to the composite tab.

TABLE I

Figure 3D:
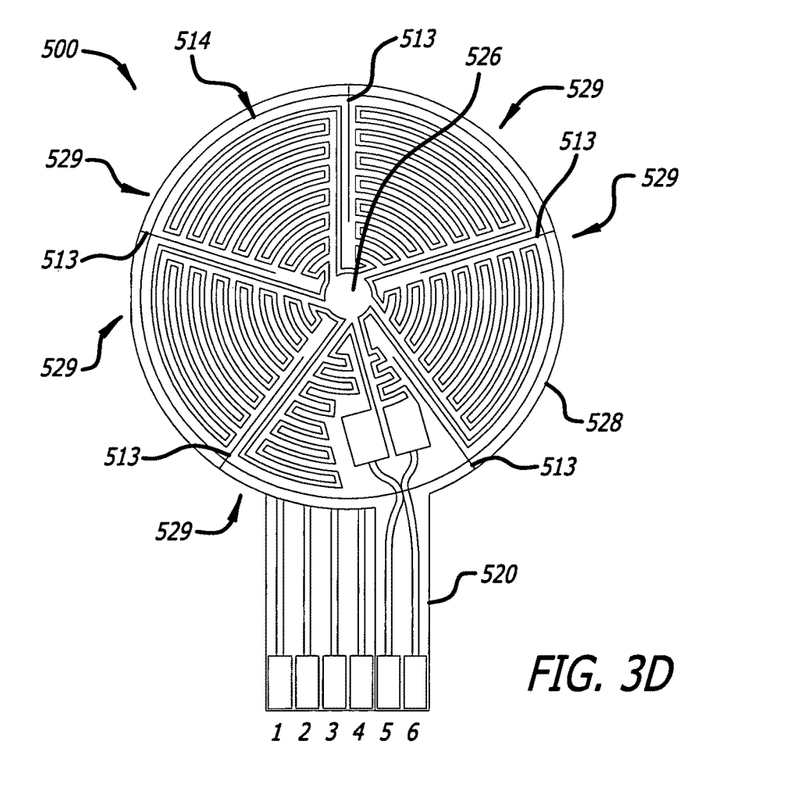

| PIN | DESCRIPTION |
|---|---|
| 1 | COPPER-OUTER THERMOCOUPLE |
| 2 | CHROMEL-OUTER THERMOCOUPLE |
| 3 | COPPER-INNER THERMOCOUPLE |
| 4 | CHROMEL-INNER THERMOCOUPLE |
| 5 | HEATER |
| 6 | HEATER |

With reference to the paddle-shaped support assembly 500 seen in FIG. 3D, the view is toward the top side; that is to say the view is toward the side that does not contact the skin region where temperature is being measured. On the top side, the heater 514 is centered on the center portion 526 of the support assembly 500. The zones of the heater form a pinwheel-like pattern whose individual blades extend from the center portion 526 toward the periphery 528 of the support assembly 500. The pinwheel configuration of the copper traces defines wedge-shaped heater zones 529 in the support assembly 500, each including a pinwheel blade trace and a slightly thicker wedge of support assembly structure underlying the trace. The slits 513 are aligned through the support assembly structure, extending entirely through the support assembly components, including the layers of substrate and thermal resistance. The slits permit the zones to move independently with respect to each other, thereby investing the support assembly 500 with additional flexibility.

Figure 3E:
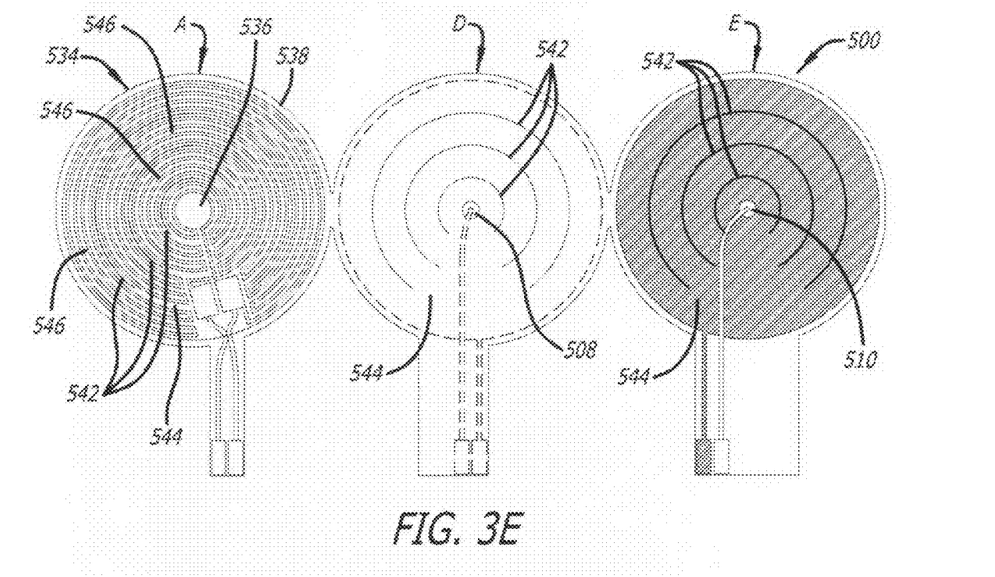
FIGS. 3E and 3F illustrate layout and assembly of a second embodiment of a thermal measurement support assembly with a multi-zone heater for a ZHF probe.
Figure 3F:
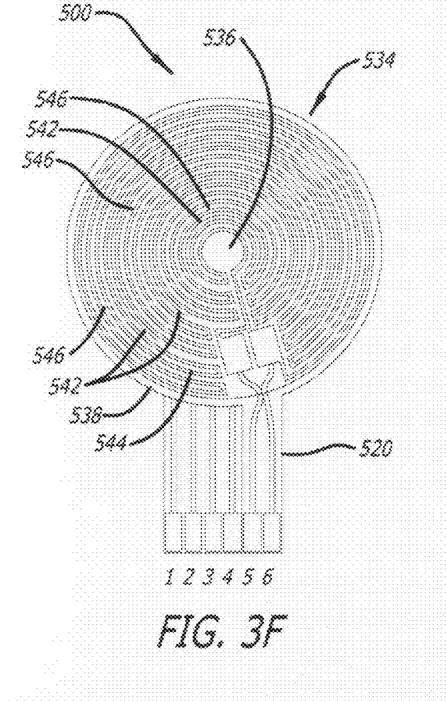

An alternate embodiment of a slitted, multi-zone support structure is shown in FIGS. 3E and 3F, where a multi-zone heater 534 is formed with partially circular or arcuate traces which increase in radius from an unheated center portion 536 to the periphery 538 of the support assembly 500. Thermocouple junctions 508 and 510 are formed as disclosed above. Partially circular or arcuate slits 542 are formed through the contiguous sections of the support assembly structure. When the sections are folded as per FIG. 3C the slits 542, are aligned so as to extend entirely through the support assembly components, including the layers of substrate and thermal resistance. The slits 542 are concentric with the disks and mutually aligned at their ends so as to define a non-slitted, generally wedge-shaped portion 544 of the support assembly 500. The slits are positioned between heater traces so as to define partially circular heater zones 546 in the support assembly 500, each including partially circular heater traces and a slightly thicker partial circle of support assembly structure underlying the traces. The slits 542 permit the partially circular heater zones to move independently with respect to each other, thereby investing the support structure with additional flexibility. Pin assignments on the tab are as per Table I.

Figure 4:
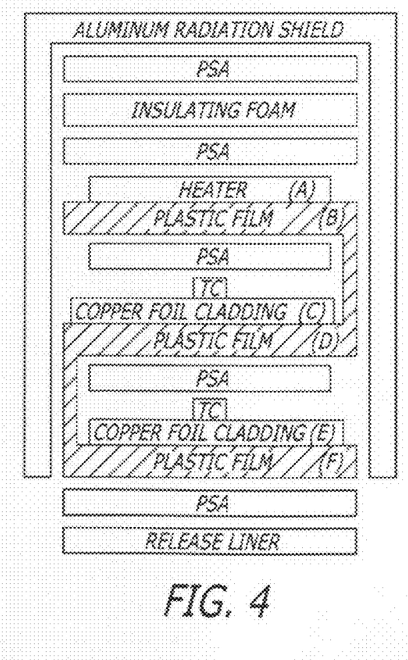
FIG. 4 sectional view in elevation showing an assembled DTT probe with the first or second support assembly embodiment.

Final assembly of a DTT probe construction with a support assembly according to the embodiments described above is illustrated in FIG. 4. In the unfolded assembly, there are three circular disks and six surface regions. Layers formed by folding the support assembly are labeled as shown in the figures. The layers are, as follows:

Major surface A is the electric heater
Major surface B is a plastic film
Major surface C is a copper layer that supports a thermal sensor
Major surface D is a plastic film
Major surface E is a copper layer that supports a thermal sensor
Major surface F is a plastic film The assembled DTT probe may include additional layers added to the structure of the probe during assembly. For example, layers of pressure-sensitive adhesive (PSA) may be disposed between the folded sections and on the top and bottom major surfaces, an insulating layer may be disposed on the layer of PSA above the heater, and a further layer of PSA may be disposed on the top of the insulating layer. Further, a release liner may be provided on the bottom PSA layer, and an aluminum radiation shield may be supported on the top PSA layer.

As per FIG. 4, the support assembly embodiments of FIGS. 3D and 3F include thermal sensors TC (thermocouples, preferably) mounted on the center portions of the top side of the support assembly sections. As the thermal sensors are mounted substantially in the centers of folded-together disks, they are vertically aligned along a central axis passing through the centers.

Figure 5A:
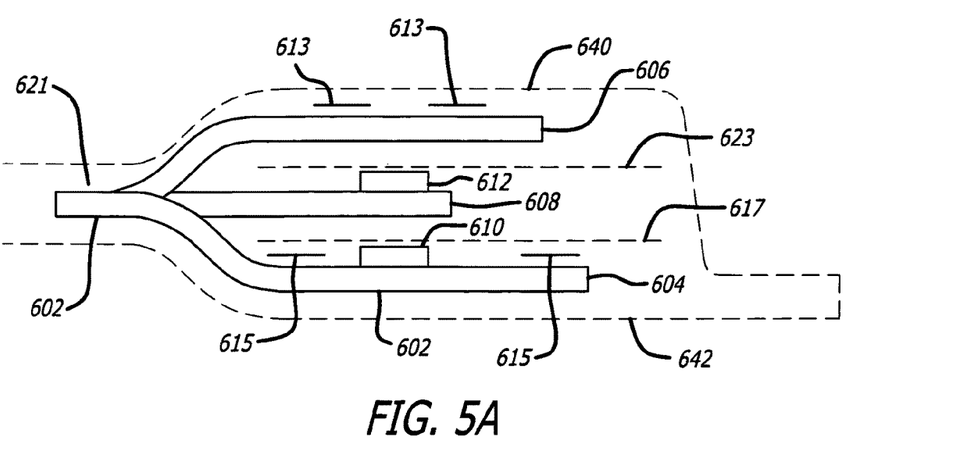
FIG. 5A is a side sectional view of a third support assembly embodiment.
Figure 5B:
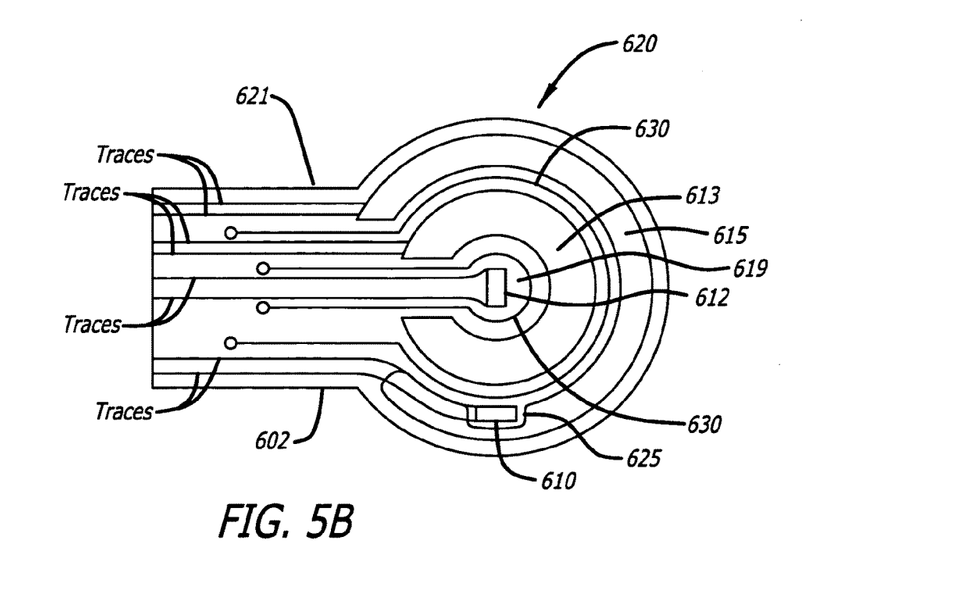
FIG. 5B is a top plan view of the third support assembly embodiment.

The third support assembly embodiment illustrated in FIGS. 5A and 5B is characterized by a structure with a single substrate layer formed into a plurality of contiguous sections that are separated into strata on which thermal sensors are disposed in a spaced-apart relationship. Preferably, the thermal sensors are disposed on separate concentric support members in a radially separated relationship. Preferably, the substrate has a paddle-like shape with nested partially circular heaters disposed thereon. At least two sensor support sections are separated by a thermally insulating layer separate from the substrate. It is desirable to provide a lead support tab projecting outwardly of the paddle's disk and supporting leads for the heaters and the thermal sensors.

With reference to FIGS. 5A and 5B, the plan view shows a flexible, two-sided substrate 602 formed into a paddle shape with a disk 620 and a tab 621. Concentric, partially circular heater traces 613 and 615 are formed on one side of the substrate 602. A notched area 625 extends into the inside edge of the outside heater trace 613. The thermal sensors 610 and 612 are disposed on the same side of the substrate 602 as the heater traces. The thermal sensor 612 is located substantially in a center portion 619 of the disk 620. The thermal sensor 610 is located in the notch 625 formed in the outermost heater trace 613. Traces for leads and pins extend along the tab 621. The substrate 602 is die-cut to form paddle-shaped slits 630 which extend through the substrate. A first slit has a partially circular section between the heater traces 613, 615 and spaced apart elongate sections along the tab 621. Another slit has a partially circular section between the innermost heater trace 615 and the center portion 619 and also includes spaced apart elongate sections along the tab 621.

As best seen in FIG. 5A, the paddle-shaped slits 630 define separable sections 604, 606, 608 of the support assembly that can be separated into strata. Preferably, the sections are separated so that the section 608 is disposed between the sections 604 and 606, and the sections 606 and 608 are disposed so that the heater 615 is positioned above the thermal sensor 612, while the heater 613 and thermal sensor 610 are positioned below the thermal sensor 612. At least one layer 617 of thermally insulating material that is separate from the substrate is interposed between the sections 604 and 606, which produces a vertical separation, and inserts a thermal resistance, between the thermal sensors 610 and 612. If necessary, a second layer 623 of thermally insulating material that is separate from the substrate 602 may also be interposed between the sections 608 and 606, which produces a vertical separation, and inserts a thermal resistance, between the thermal sensor 612 and the heater 615. A flexible layer of insulating material 640 is applied by pressure sensitive adhesive to the section 606, over the heater 613, and a layer of patient adhesive 642, with a removable backing is applied to the bottom of the section 604.

A support assembly according to any of the embodiments disclosed herein may be constructed using a substrate constituted of a single double-sided sheet of plastic film such as Kapton® polyimide, Kaptrex® polyimide, polyester or another film of flexible, thermally insulating material. The sheet may be coated on one or both sides with a copper film and various elements such as heaters, copper disks, and copper leads and pins may be made by photo-etching before the support assembly is folded or separated. The sheet may then be die-cut to the required shape and folded or separated as described above. Other metals with high thermal conductivities, like gold or aluminum, may also be used, although copper is preferred because it can form one half of a T-type thermocouple; however, other types of thermocouples are possible, and it may be possible to dispense with metal films altogether if other thermal sensors such as balanced RTD's, thermistors, and/or point junction thermocouples are used to measure temperature. Chromel traces and leads may be formed by deposition, or by peening.

A disposable DTT probe may be easily and inexpensively made using the support assembly construction embodiments described above. Disposability makes the commercialization of a DTT probe possible. Also, a single-use probe limits the potential for cross-contamination and makes it possible for more patients to benefit from perioperative temperature monitoring.

Although the invention has been described with reference to the presently preferred embodiment, it should be understood that various modifications can be made without departing from the spirit of the invention. Accordingly, the invention is limited only by the following claims.

The invention claimed is:

1. A support assembly for a deep tissue temperature probe, comprising:
 a substrate with two sides;
 a plurality of sections defined in the substrate, in which each section is joined to at least one adjacent section at a peripheral location common to both sections;
 a first thermal sensor and a second thermal sensors, each supported on a respective one of two adjacent sections;
 a heater supported on the substrate; and,
 a pattern of slits in one of the two adjacent sections, wherein each of the pattern of slits comprises an opening extending within and through the substrate, wherein the pattern of slits in the one of the two adjacent sections includes at least three slits.

2. The support assembly of claim 1, wherein the first thermal sensor is mounted on a surface of a first section of the two adjacent sections, the second thermal sensor is mounted on a surface of a second section of the two adjacent sections, each section of the two adjacent sections has a pattern of slits, the pattern of slits define a plurality of zones in the heater, and the sections are capable of being folded together such that the slits are aligned and open through all of the sections.

3. The support assembly of claim 2, wherein the zones are wedge shaped and the slits are radial slits.

4. The support assembly of claim 2, wherein the zones are arcuately shaped and the slits are arcuately-shaped slits.

5. The support assembly of claim 2, wherein the zones are partially circular and the slits are partially circular slits.

6. A support assembly for a deep tissue temperature probe, comprising:
 a flexible substrate with at least two sections;
 a plurality of zones defined in one of the sections;
 two thermal sensors, each supported on a respective one of two adjacent sections, at least one of the sections having a pattern of slits, wherein the pattern of slits includes at least three slits, wherein each of the pattern of slits comprises an openings extending within and through the substrate; and,
 a heater supported on the flexible substrate and including a heater zone positioned on each of the plurality of zones.

7. The support assembly of claim 6, wherein the plurality of zones are wedge shaped and form a pinwheel configuration in which each zone is flexible independently of the other one of the plurality of zones.

8. The support assembly of claim 6, wherein the zones are arcuately shaped and each zone is flexible independently of any other zone.

9. The support assembly of claim 6, wherein the zones are partially circularly shaped and each zone is flexible independently of any other zone.

* * * * *